US012299044B2

(12) United States Patent
Krishnaprasad et al.

(10) Patent No.: US 12,299,044 B2
(45) Date of Patent: May 13, 2025

(54) PERSONALIZED HEALTH SEARCH ENGINE

(71) Applicant: UnitedHealth Group Incorporated, Minnetonka, MN (US)

(72) Inventors: Vidhya Krishnaprasad, Monmouth Junction, NJ (US); Amanda R. Hoppock, Port Saint Lucie, FL (US); Mary E. Ayala, Ellsworth, WI (US); Erin M. Moore, Haubstadt, IN (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 11 days.

(21) Appl. No.: 17/658,221

(22) Filed: Apr. 6, 2022

(65) Prior Publication Data

US 2023/0325441 A1 Oct. 12, 2023

(51) Int. Cl.
*G06F 16/9032* (2019.01)
*G16H 70/60* (2018.01)

(52) U.S. Cl.
CPC ....... *G06F 16/90324* (2019.01); *G16H 70/60* (2018.01)

(58) Field of Classification Search
None
See application file for complete search history.

(56) References Cited

U.S. PATENT DOCUMENTS

| 8,527,291 | B1 | 9/2013 | Kochendorfer |
| 8,793,265 | B2 | 7/2014 | Song et al. |
| 9,323,844 | B2 | 4/2016 | Kasterstein et al. |
| 10,204,163 | B2 | 2/2019 | Gao et al. |
| 10,713,289 | B1* | 7/2020 | Mishra ............... G06F 40/30 |
| 2005/0071328 | A1 | 3/2005 | Lawrence |
| 2009/0070318 | A1* | 3/2009 | Song ............... G06F 16/9535 707/999.005 |
| 2009/0076846 | A1 | 3/2009 | Bentwich et al. |
| 2009/0327270 | A1 | 12/2009 | Teevan et al. |
| 2011/0196886 | A1* | 8/2011 | Ho ............... G16H 30/20 707/769 |
| 2011/0270843 | A1 | 11/2011 | Albin |

(Continued)

OTHER PUBLICATIONS

Ertugrul et al., "A survey on semanticized and personalized health recommender systems", Expert Systems, vol. 37, Dec. 13, 2019, 23 pp.

(Continued)

*Primary Examiner* — Giuseppi Giuliani
(74) *Attorney, Agent, or Firm* — Shumaker & Sieffert, P.A.

(57) ABSTRACT

Example devices and techniques are described for personalizing a health-related search. An example computing device includes a memory and one or more processors circuitry. The memory is configured to store a search query. The one or more processors are configured to obtain the search query and determine that the search query is health related. The one or more processors are configured to, based on the determination that the search query is health related, determine a subject of the search query. The one or more processors are configured to determine health information of the subject of the search query. The one or more processors are configured to modify, based on the health information of the subject of the search query, at least one of the search query or an order of search results, and present the search results or the modified search results to the user.

14 Claims, 6 Drawing Sheets

(56) References Cited

U.S. PATENT DOCUMENTS

| | | | |
|---|---|---|---|
| 2011/0313994 A1 | 12/2011 | Varshavsky et al. | |
| 2016/0147960 A1* | 5/2016 | Kim | G16H 50/70 |
| | | | 705/3 |
| 2017/0140008 A1* | 5/2017 | Ramaswami | G16H 50/20 |
| 2020/0159848 A1* | 5/2020 | Yeo | G06N 20/00 |
| 2021/0064628 A1* | 3/2021 | McNeil | G16H 50/20 |
| 2022/0068462 A1* | 3/2022 | Dolan | G10L 25/63 |

OTHER PUBLICATIONS

Hochberg et al., "Assessment of the Frequency of Online Searches for Symptoms Before Diagnosis: Analysis of Archival Data", Journal of Medical Internet Research, vol. 22, No. 3, JMIR Publications, Jun. 3, 2020, 7 pp., https://www.jmir.org/2020/3/e15065.

Zheng et al., "How Do Healthcare Professionals Personalize Their Software? A Pilot Exploration Based on an Electronic Health Records Search Engine", MEDINFO 2019: Health and Wellbeing e-Networks for All, vol. 264, International Medical Informatics Association (IMIA) and IOS Press, Aug. 2019, pp. 1408-1412.

\* cited by examiner

```
                                                    ┌─ 40
┌─────────────────────────────────────────────┐
│  YES, YOU ARE HAVING A HEART ATTACK SEEK    │
│         IMMEDIATE MEDICAL ATTENTION         │
│                                             │
│   A HEART ATTACK MAY LEAD TO DEATH IF NOT   │
│              TREATED PROMPTLY               │
│                                             │
│   HEART ATTACK SYMPTOMS INCLUDE CHEST PAIN  │
│                                             │
```
```
│                                             │
│   GERD MAY CAUSE SYMPTOMS SIMILAR TO A HEART│
│                    ATTACK                   │
│                                             │
│         GERD MAY CAUSE CHEST PAIN           │
└─────────────────────────────────────────────┘
```

FIG. 4A

```
                                                    ┌─ 40'
┌─────────────────────────────────────────────┐
│   GERD MAY CAUSE SYMPTOMS SIMILAR TO A HEART│
│                    ATTACK                   │
│                                             │
│       ACID REFLUX  MAY CAUSE CHEST PAIN     │
│                                             │
```
```
│                                             │
│   HEART ATTACK SYMPTOMS INCLUDE CHEST PAIN  │
│                                             │
│   A HEART ATTACK MAY LEAD TO DEATH IF NOT   │
│              TREATED PROMPTLY               │
│                                             │
│   YES, YOU ARE HAVING A HEART ATTACK.  SEEK │
│         IMMEDIATE MEDICAL ATTENTION         │
└─────────────────────────────────────────────┘
```

FIG. 4B

PERSONALIZED HEALTH SEARCH ENGINE

TECHNICAL FIELD

This disclosure relates to search engines, and in particular personalized health search engines.

BACKGROUND

Various search engines exist which may be used to search the Internet for information. Typically, a user may enter search terms into a search engine. The search engine then may search websites, databases, and the like connected to the Internet using the entered search terms. As each search engine may use different algorithms to search the Internet based on the search terms, each search engine may generate search results in a different manner and present the search results back to the user.

SUMMARY

Existing Internet search engines may rely on the user to type the appropriate search terms into the search engine. However, when a user enters health search terms, such as symptoms that they, or one they are searching on behalf of, the search results may present the user with potential causes of the symptoms that may be far off of what they may be experiencing. For example, a 25-year-old in good cardiac health, without a family history of heart disease, but with gastroesophageal reflux disease (GERD) who has just been exercising may experience chest pain. When that person enters chest pain as search terms, the search engine may present heart attack as the first search result, while it is much more likely the pain is being caused by GERD. This may cause concern, stress, and anxiety in the user. The user may even be told in the search results that they are suffering a heart attack and should seek immediate medical attention. Such results may cause the user to call an ambulance, go to an emergency room, or go to an urgent care center. Thus, the execution of the search and the presentation of the search results may unnecessarily increase healthcare costs, increase the burden on the health system, and waste healthcare resources that may be better directed to patients with more urgent conditions than the user may have.

Therefore, it may be desirable to have a personalized health search engine. The personalized health search engine may be different than existing search engines. For example, the personalized health search engine may, prior to executing the search, add additional search terms. Such additional search terms may be based on information personal to the user or the living being for whom the user is searching. This personal information may include personal healthcare data (for example, from electronic healthcare records or electronic medical records), prescription data, previous search data, sensor data, exercise data, diet data, publicly available data, social media posts or likes, insurance claims, etc. As used herein, the term "personal" is meant to encompass not only information that is related to a person, but also information that is related to another type of living being, such as an animal, in the case that the subject of the search is an animal. For example, a user may be searching the Internet to find information about a health condition of their pet. In another example, the personalized health search engine may order or re-order the search results prior to presenting them to the user. As used herein, "order" includes ordering for the first time or re-ordering of search results that have been previously ordered. Such ordering may be based on information personal to the user or the living being for whom the user is searching. In some examples, the personalized health search engine may both add search terms and order the search results as described herein In this manner, the results presented to the user may be personalized for the user or living being for whom the user is searching and may reduce anxiety in the user and reduce unnecessary health care burdens and costs as the user may be presented with the best results first for the user or the living being for whom the user is searching, rather than the best results being buried deep within the search results. In some examples, the personalized health search engine is implemented as an entire search engine. In other examples, the personalized heath search engine is implemented as an add-on application to an existing search engine.

In one example, this disclosure describes a method including: obtaining, by one or more processors, a search query, the search query comprising one or more search terms; determining, by the one or more processors, that the search query is health related; based on the determination that the search query is health related, determining, by the one or more processors, a subject of the search query, the subject of the search query being a living creature for whom a search is being performed; based on the determination of the subject of the search query, determining, by the one or more processors, health information of the subject of the search query; modifying, by the one or more processors and based on the health information of the subject of the search query, at least one of the search query to generate a modified search query or an order of search results to generate modified search results; and presenting, by the one or more processors, the search results or the modified search results to the user.

In another example, this disclosure describes a computing system that includes: a memory configured to store a search query comprising one or more search terms; and one or more processors implemented in circuitry and communicatively coupled to the memory, the one or more processors being configured to obtain the search query; determine that the search query is health related; based on the determination that the search query is health related, determine a subject of the search query, the subject of the search query being a living creature for whom a search is being performed; based on the determination of the subject of the search query, determine health information of the subject of the search query; modify, based on the health information of the subject of the search query, at least one of the search query to generate a modified search query or an order of search results to generate modified search results; and present the search results or the modified search results to the user.

In another example, this disclosure describes a non-transitory computer-readable storage medium encoded with instructions that, when executed, cause one or more processors of a computing device to: obtain a search query; determine that the search query is health related; based on the determination that the search query is health related, determine a subject of the search query, the subject of the search query being a living creature for whom a search is being performed; based on the determination of the subject of the search query, determine health information of the subject of the search query; modify, based on the health information of the subject of the search query, at least one of the search query to generate a modified search query or an order of search results to generate modified search results; and present the search results or the modified search results to the user.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 4A-4B are conceptual diagrams illustrating examples of search results and personalized search results according to one or more aspects of this disclosure.

DETAILED DESCRIPTION

Figure 1:
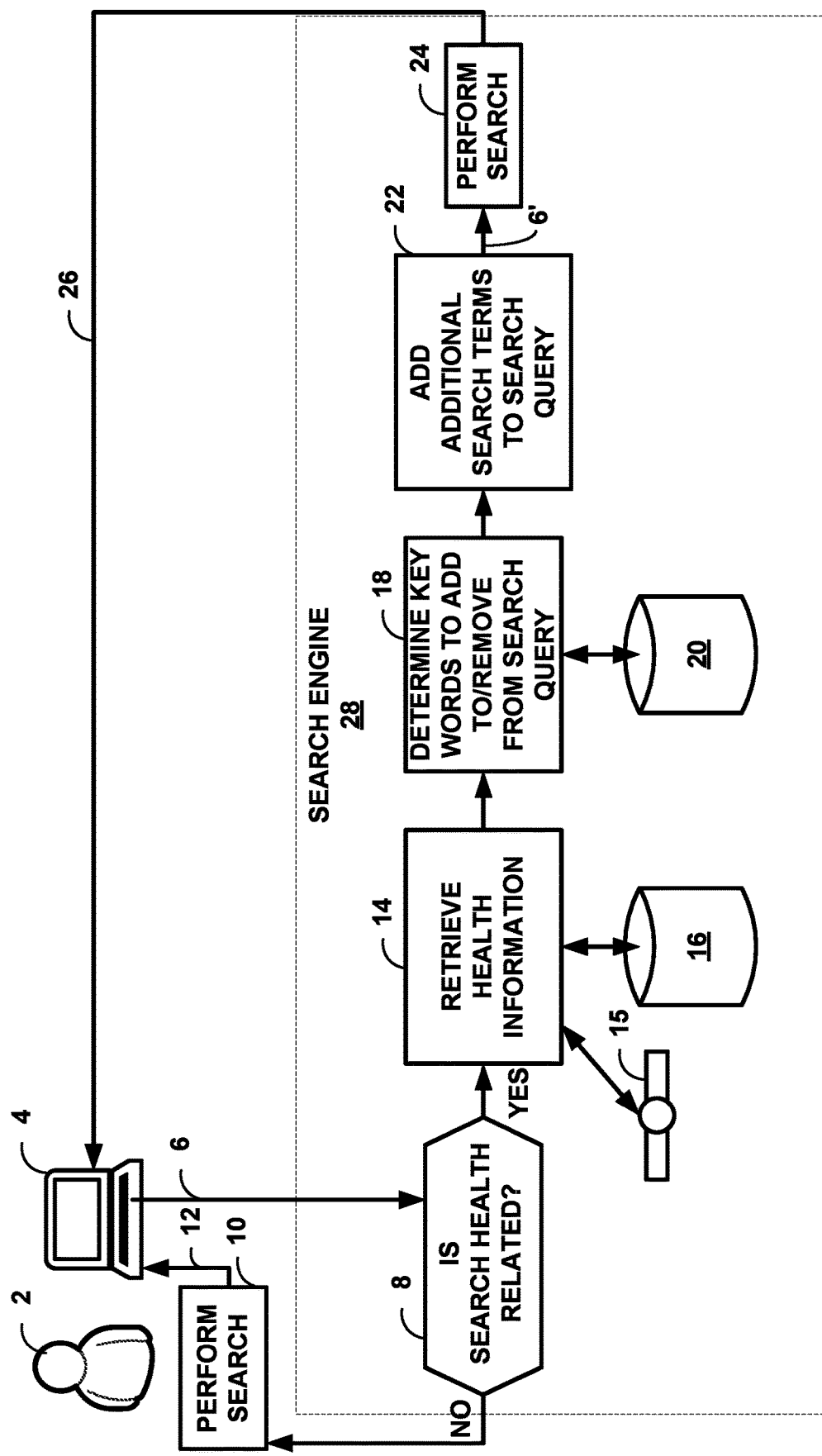
FIG. 1 is a conceptual diagram illustrating example techniques for adding search terms to a search query according to one or more aspects of this disclosure.

When people feel sick or otherwise are worried about health symptoms they may be feeling or their loved ones may be feeling, they often turn to the Internet to research their symptoms. Indeed, surveys show that seventy percent of Internet users report searching for health information online and more than a third attempt to self-diagnose their health condition. However, often such searching can be quite stressful and anxiety inducing for the searcher.

Without personal health information, search engines select and sequence search results according to general purpose algorithms based on phrase matching, advertising, and/or fees paid to highlight certain websites. Thus, the results of health-related searches are often unhelpful and, in some cases, may even be misleading. For example, the vast quantity of health information which exists on the Internet might be educational, however search results containing multiple potential causes for symptoms may provide a user with a larger number of medical conditions for the user to be concerned about, even when such conditions are unlikely to be the cause of the symptoms. This may cause stress and anxiety in the user. If the conditions returned in the search results (especially if they are at the top of the search results) are deemed serious or urgent enough, the search results may convince the user to seek immediate medical attention, such as call an ambulance, go to an emergency room, or go to an urgent care clinic. This may be wasteful of money and medical resources if the user (or someone a user is searching for) does not actually suffer from the medical condition returned in the search results.

Current health specific search engines may use some additional minimal information, such as demographics or symptoms which must be entered manually be a user. However, such health specific search engines do not select or sort search results and do not personalize the search output based on access to personal heath data. For example, some health specific search engines merely search a specific website (as opposed to the Internet) for keywords or search terms in the search query. Other health specific search engines may include a 'symptom checker' that requires the user to enter in data about themselves manually and does not save, store, or otherwise use data from additional sources.

As such, it may be useful to have a personalized health search engine that may search the Internet and return search results that are 1) more relevant to the health situation of the user or the living being for whom the user is searching; and/or 2) ordered in a manner that places more likely causes of the symptoms being searched at the top of the search results without requiring a user to manually enter all available health data. The personalized health search engine may make use of, not only the search terms entered by the user, but also personal health information of the user or the living being for whom the user is searching to generate and/or order more relevant results for the user or the person for whom the user is searching. Either or both of such features of the personalized health search engine may be implemented in a search engine or as an add-on application to an existing search engine.

In some examples, the personalized health search engine may add in additional search terms to the search query based on personal health information. In some examples, the personalized health search engine may order search results based on personal health information. In some examples, the personalized health search engine may both add in additional search terms to the search query based on personal health information and order search results based on personal health information. As such, the search results presented to the user may be more useful as the search results may be more relevant to the user or the living being for whom the search is being performed.

The techniques of this disclosure may improve the appropriate utilization of emergency services, emergency rooms, and urgent care facilities and reduce the unnecessary utilization of emergency services, emergency rooms, and urgent care facilities for non-critical health situations. This may result in cost savings and better use of medical resources for serving truly critical needs. The techniques of this disclosure may also increase patient confidence in data used to determine their own plan of care by providing them with more relevant information for their health situation. For example, the techniques of this disclosure may facilitate an increase in patient self-monitoring, self-control of health which can lead to patients living healthier lives, which may result in further cost savings and a higher quality of life. The techniques of this disclosure may increase the consistency of health-related searches across the continuum of care and across multiple users in the care of one caregiver or across multiple caregivers of one individual, which may drive stronger collaboration and understanding of the patient's condition. The techniques of this disclosure also improve the functioning of a computing device (e.g., a computer) by providing better, personalized health-related search results and/or by providing more relevant health-related search results at or near the top of the health-related search results rather than much later in the search results where a user is unlikely to review the more relevant health-related search results.

FIG. 1 is a conceptual diagram illustrating example techniques for adding search terms to a search query according to one or more aspects of this disclosure. While in the example of FIG. 1, search engine 28 is depicted as an add-on application to an existing search engine, in other examples, search engine 28 may be a stand-alone search engine and may perform or execute Internet searches. FIG. 1 depicts user 2 and computing device 4. Computing device 4 may be a laptop computer, a desktop computer, a smart phone, a tablet, a wearable device, an Internet of Things device (such as a personal assistant (e.g., a smart speaker), a smart television, etc.) or another computing device capable of obtaining search terms for search query 6 from user 2. User 2 may use computing device 4 to enter search query 6 to search the Internet. In some examples, user 2 may enter search query 6 for themselves, for example the search query might be "Am I having a heart attack?" In some examples, user 2 may enter the search query for another living being. For example, user 2 may enter the search query for another human being, an animal, such as a pet or service animal, or the like.

For example, user 2 may enter search query 6 "Am I having a heart attack" into search engine 28 via a user interface of computing device 4. In some examples, search engine 28 may be resident on computing device 4. In other examples, search engine 28 may be based on a cloud computing platform. In some examples, a portion of search engine 28 may be resident on computing device 28 and a portion of search engine 28 may be based on the cloud computing platform. In some examples, search engine 28 is an add-on to an existing search engine, for example, a web browser plug-in. In some examples, search engine 28 is a stand-alone search engine.

Search engine 28 may determine whether search query 6 is health related (8). For example, search engine 28 may use a natural language processing engine to determine if search query 6 is health related. The natural language processing engine may be configured to discern between health-related words and non-health-related words. In some examples, search engine 28 may look up the search terms in a database or lookup table (not shown in FIG. 1) of health-related terms, such as symptoms, diseases, medical conditions, context terms, such as "feel," etc., to determine if search query 6 is health related. If search engine 28 is an add-on application to an existing search engine rather than built-in functionality of a search engine, search engine 28 may intercept the search query from the existing search engine prior to determining if search query 6 is health related so that the search is not performed until it is determined whether search query 6 is health related.

If search query 6 is not health related (the "NO" path from box 8), search engine 28 (or the search engine to which search engine 28 is an add-on) may perform the search (10) and return search results 12 to user 2 via computing device 4. In this example, because the search is not health related, search engine 28 need not add search terms to search query 6 or order search results 12 based on health information of user 2 or a living being for which the search is being performed.

If search query 6 is health related (the "YES" path from box 8), search engine 28 may retrieve personal health information (14). As part of retrieving personal health information, search engine 28 may determine whether search query contains any search terms referring to user 2 or another living being. For example, if search query 6 is "Am I having a heart attack", search engine 28 may determine that user 2 is inquiring for themselves and not on the behalf of another living being. For example, computing device 4 may be a device that is personal to user 2 or a device most often used by user 2. If computing device 4 is a communal computing device, search engine 28 may prompt user 2 to enter their name. If search query 6 is "Is my father having a heart attack," search engine 28 may prompt user 2 to enter their father's name. If search query 6 is "Does my dog have heartworms," search engine 28 may prompt user 2 to enter their dog's name. User 2 may then enter additional information, such as a name, that will facilitate search engine 28 in obtaining personal health information of the subject of the search. While not shown in FIG. 1, in some examples, if search query 6 is disassociated with any individual, such as "What are the symptoms of a heart attack," search engine 28 may not retrieve personal health information and search engine 28 (or the search engine to which search engine 28 is an add-on) may perform the search (10)).

Turning back to the example where search query 6 is "Am I having a heart attack," because "heart attack" is a health condition, and "I" indicates self, the natural language processing engine may determine that search query 6 is a health-related query and refers to user 2. Search engine 28 may retrieve personal health information (14) which is specific to the living being for whom the search is being conducted (also referred to as the "subject of the search query"), in this example, user 2. In some examples, search engine 28 may use a lookup table to determine what data may be important for that health condition. For example, in case of a query about a heart attack, one may want to include any health information relating to the heart and/or any other health information that may present similar symptoms to a heart attack, such as acid reflux. Therefore, search engine 28 may retrieve from one or more databases 16, sensor(s) (such as sensor 15 which may include a smartwatch, a fitness monitor, a wearable medical device, or an implantable medical device), webpages (such as social media sites (not shown in FIG. 1)), and/or browsing history (not shown in FIG. 1) any such health information. In some examples, as used herein, health information may include any available information relating to the heath of user 2 or the living being for whom the search is being performed. Examples of health information include data from electronic medical records, electronic health records, pharmacy data, claims data (e.g., health insurance claims data, Medicare data, prescription insurance claims data, etc.), family health history, demographic data including social determinants of health (SDOH) (e.g., conditions in the environment where the living being lives, works, was born, etc.), biometric data from sensors, online activity (such as posts to social media and previous searches), and the like. Sensor data, such as data from sensor 15, may be referred to herein separately as "biometric sensor data." In some examples, search engine 28 may not retrieve all the health data of user 2 or the living being for whom the search is being performed, but may retrieve any relevant health data that is available to search engine 28. For example, if user 2 has not given permission for search engine 28 to access their EMRs and search engine 28 is configured to require permission to access EMRs, search engine 28 may not retrieve health information from EMRs.

Search engine 28 may determine keywords to add to and/or remove from search query 6 (18) based on the retrieved personal health information. For example, for example, if user 2 previously searched for a brand of antacid or proton pump inhibitor, search engine 28 may determine that user 2 may suffer from acid reflux and determine to add the search terms "acid reflux" to search query 6 and/or remove "attack" from search query 6, as a heart attack may not be likely to be the cause of the symptoms, but heart burn may be the cause. In some examples, search engine 28 may retrieve the additional search terms from one or more databases 20. One or more databases 16 and one or more databases 20 may be the same databases, different databases, or overlapping databases. In some examples, one or more databases 20 may be implemented as one or more lookup tables.

For example, search engine 28 may identify diagnoses and other health conditions exhibited by the subject of search query 6 that could cause similar symptoms to the symptoms being searched or the symptoms of the medical condition being searched. For example, search engine 28 may identify key phrases in the written portion of the health information of the subject of the search that correspond to any diagnosis or other health condition. Search engine 28 may compare such key phrases to terms in the lookup table listing what data may be important for the health condition or symptoms being searched (e.g., a heart attack). Search engine 28 may assign health conditions appearing in both lists a higher likelihood of causing the symptoms. For example, if acid reflux is the only health condition user 2 has that presents similar symptoms to a heart attack, search engine 28 may add "acid reflux" to search query 6.

Search engine 28 may also assess any relevant biometric sensor data to determine likelihood of potential causes of the symptoms relating to search query 6. For example, if sensor 15 senses heart rhythm data of user 2, and heart attacks are one of the potential causes of chest pain, search engine 28 may retrieve the heart rhythm data of user 2. If search engine 28 finds no indicators of an abnormal heart rhythm in the heart rhythm data of user 2, search engine 28 may deprioritize the "heart attack" search terms in search query 2 (for example, move them to the end of search query 6 after any added search terms) or, in some examples, remove the search terms completely.

Search engine 28 may add additional search terms to search query 6 (22). For example, search engine 28 may add "acid reflux" to "Am I having a heart attack." Search engine 28 may add the additional search terms at any position in search query 6 to generate search query 6'. For example, search engine 28 may add the additional search terms to the beginning of search query 6, to the end of search query 6, or at any other position in search query 6. For example, search query 6' may be "Am I having a heart attack acid reflux." In the case where search engine 28 is a stand-alone search engine, search engine 28 may perform the search (24) on search query 6'. If search engine 28 is a complete search engine, rather than an add on, search engine 28 may perform the search (24) on search query 6'. In the case where search engine 28 is an add-on application to an existing search engine, search engine 28 may hand off the search to the existing search engine which may perform the search (24) on search query 6'.

Once the search is performed, the existing search engine or search engine 28 may provide personalized search results 26 to user 2 via computing device 4. For example, because search query 6' included the search terms "acid reflux," user 2 may receive personalized search results 26 including hits for heart burn as well as heart attacks, rather than only (or primarily) heart attacks.

According to the techniques of this disclosure, search engine 28 may obtain search query 6. Search engine 28 may determine that search query 6 is health related. In response to the determination that the search query is health related, search engine 6 may determine a subject of search query 6, the subject of the search query being a living creature for whom a search is being performed. In response to the determination of the subject of search query 6, search engine 28 may determine health information of the subject of search query 6 (e.g., user 2). Search engine 28 may modify, based on the health information of the subject of search query 6, search query 6 to generate a modified search query (e.g., personalized search query 6') or an order of search results to generate modified search results. Search engine 28 may present search results 26 or the modified search results to user 2.

Figure 2A:
FIGS. 2A-2B are conceptual diagrams illustrating examples of a search query and a personalized search query according to one or more aspects of this disclosure.
Figure 2B:

FIGS. 2A-2B are conceptual diagrams illustrating examples of a search query and a personalized search query according to one or more aspects of this disclosure. FIG. 2A shows an example search query 6 in which user 2 has entered, via a user interface of computing device 4, the search terms "Am I having a heart attack?" Applying the techniques of FIG. 1, search engine 28 may add additional search terms to search query 6 prior to conducting the search or prior to having the search conducted based on the personal health information of, in this example, user 2 because user 2 is the subject of search query 6. For example, search engine 28 may add the terms "heart burn" to search query 6 as shown in search query 6' of FIG. 2B.

Figure 3:
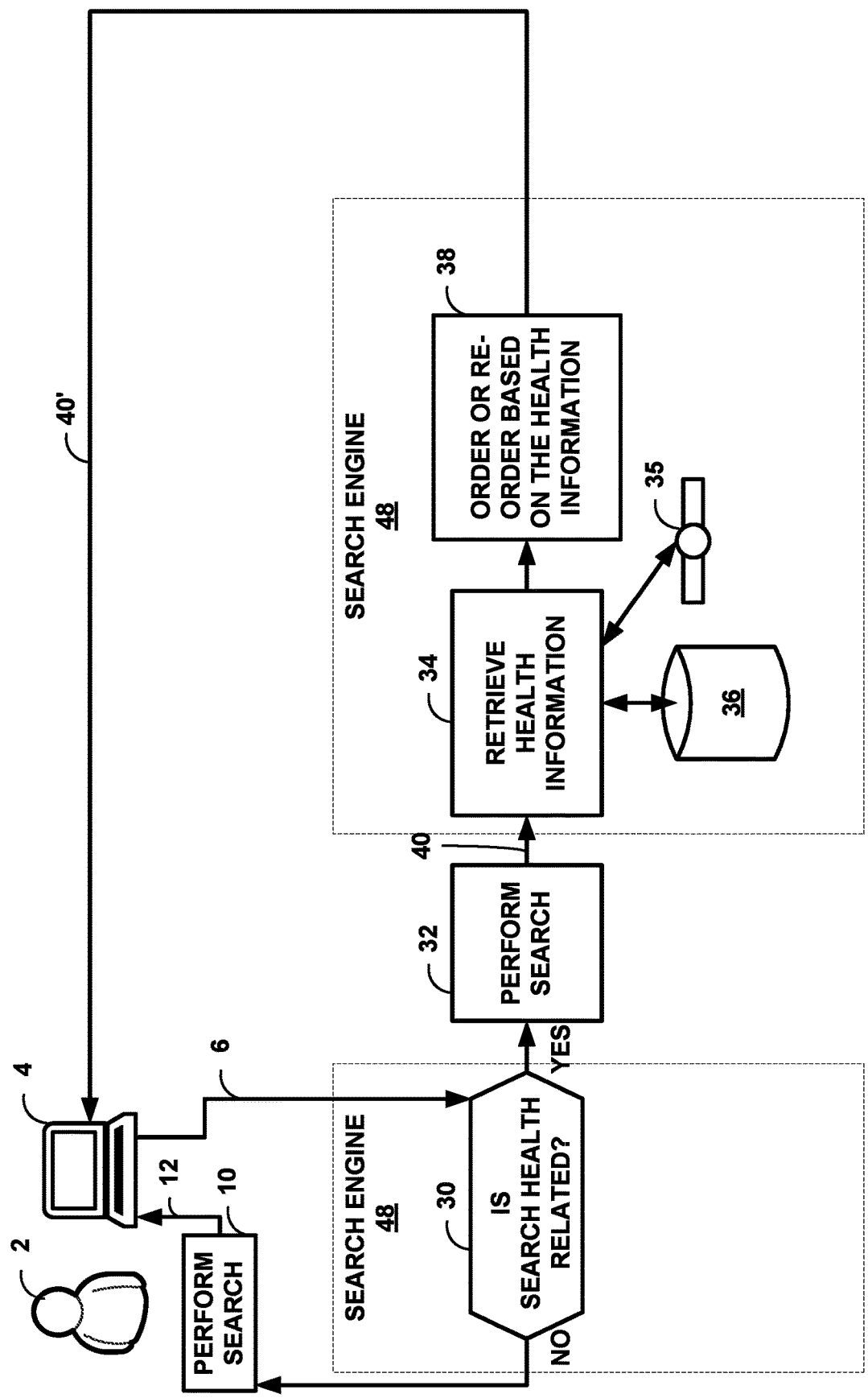
FIG. 3 is a conceptual diagram illustrating example techniques for ordering search results according to one or more aspects of this disclosure.

FIG. 3 is a conceptual diagram illustrating example techniques for ordering search results according to one or more aspects of this disclosure. The techniques of FIG. 3 may be used on their own or in combination with the techniques of FIG. 1. While in the example of FIG. 3, search engine 48 is depicted as an add-on application to an existing search engine, search engine 48 may be a stand-alone search engine and may perform or execute Internet searches.

As in FIG. 1, FIG. 3 depicts user 2 and computing device 4. User 2 may use computing device 4 to enter search query 6 to search the Internet. In some examples, user 2 may enter search query 6 for themselves, for example the search query might be "Am I having a heart attack." In some examples, user 2 may enter the search query for another living being. For example, user 2 may enter the search query for another human being, an animal, such as a pet or service animal, or the like.

For example, user 2 may enter search query 6 "Am I having a heart attack" into search engine 48 via a user interface of computing device 4. In examples where the techniques of FIG. 1 and FIG. 3 are used together, search engine 48 may be an example of search engine 28 or may be a separate application from search engine 28. In some examples, search engine 48 may be resident on computing device 4. In other examples, search engine 48 may be based on a cloud computing platform. In some examples, a portion of search engine 48 may be resident on computing device 4 and a portion of search engine 48 may be based in the cloud. In some examples, search engine 48 is an add-on to an existing search engine. In some examples, search engine 48 is a stand-alone search engine.

Search engine 48 may determine whether search query 6 is health related (30). For example, search engine 48 may use a natural language processing engine to determine if search query 6 is health related. The natural language processing engine may be configured to discern between health-related words and non-health-related words. In some examples, search engine 28 may look up the search terms in a database (not shown in FIG. 3) of health-related terms, such as symptoms, diseases, medical conditions, context terms, such as "feel," etc., to determine if search query 6 is health related. If search engine 48 is an add-on application to an existing search engine rather than built-in functionality of a search engine, search engine 48 may intercept the search query from the existing search engine prior to determining if search query 6 is health related so that the search is not performed until it is determined whether search query 6 is health related.

If search query 6 is not health related (the "NO" path from box 30), search engine 48 (or the search engine to which search engine 48 is an add-on) may perform the search (10) on the original search query 6 and return search results 12 to user 2 via computing device 4. In this example, because the search is not health related, search engine 48 need not add search terms to search query 6 or order search results 12 based on health information of user 2 or a living being for which the search is being performed.

If search query 6 is health related (the "YES" path from box 30), and search engine 48 is a stand-alone search engine, search engine 48 may perform the search (32) on search query 6. For example, user 2 may enter search query 6 as "Am I having a heart attack." Because a heart attack is a health condition and "I" indicates user 2, a natural language processing engine of search engine 48 may determine that search query 6 is a health-related query and refers to user 2.

If search engine 48 is an add-on application to an existing search engine, search engine 48 may prompt the existing search engine to perform the search (32) on search query 6. However, if the techniques of FIG. 3 are used together with the techniques of FIG. 1, the search terms of search query 6 may be augmented with additional search terms, as set forth in the example of FIG. 1, to generate a search query 6' prior to performing the search or prompting an existing search engine to perform the search.

In the example where search engine 48 is an add-on application for an existing search engine, search engine 48 may intercept search results 40 prior to search results 40 being provided to user 2 via computing device 4. Search engine 48 may retrieve health information specific to the living being for whom the search is being performed (34). For example, search engine 48 may use a lookup table to determine what health data is important for that health condition. For example, in case of a search query relating to a heart attack of user 2, one might want to know if user 2 had recent physical activity, heart burn conditions, and/or family history of heart disease. In some examples, search engine 48 may retrieve from one or more databases 36, sensor(s) (such as sensor 35 which may include a smartwatch, a fitness monitor, a wearable medical device, or an implantable medical device), webpages (such as social media sites (not shown in FIG. 3)), and/or browsing history (not shown in FIG. 3) any available personal health information.

For example, search engine 48 may identify diagnoses and other health conditions exhibited by the subject of search query 6 that could cause similar symptoms to the symptoms being searched or the symptoms of the medical condition being searched. For example, search engine 48 may identify key phrases in the written portion of the health information of the subject of the search that correspond to any diagnosis or other health condition. Search engine 48 may compare such key phrases to terms in the lookup table listing what data may be important for the health condition or symptoms being searched (e.g., a heart attack). Search engine 48 may assign health conditions appearing in both lists a higher likelihood of causing the symptoms. Search engine 48 may use this likelihood information when ordering search results 40 to generate personalized search results 40'.

Search engine 28 may also assess any relevant biometric sensor data to determine likelihood of potential causes of the symptoms relating to search query 6. For example, if sensor 35 senses heart rhythm data of user 2, and heart attacks are one of the potential causes of chest pain, search engine 48 may retrieve the heart rhythm data of user 2. If search engine 48 finds no indicators of an abnormal heart rhythm in the heart rhythm data of user 2, search engine 48 may deprioritize the "heart attack" when creating personalized search results 40'. For example, search engine 48 may move search results related to heart attacks to a position after the search results related to GERD.

Search engine 48 may order search results 40 based on the retrieved personal health information to generate personalized search results 40' which may be in a different order than search results 40. For example, search engine 48 may retrieve any available personal health information, clinical data, biometric sensor data, or the like, for user 2 that may be relevant to the symptoms user 2 is experiencing or the condition for which user 2 is searching. In the example where the techniques of FIG. 3 are used together with the techniques of FIG. 1, this step may occur earlier as the personal health information may already have been retrieved. For example, biometric sensor data may indicate that user 2 just finished a high intensity physical activity. Other personal health information may indicate that user 2 suffers from heart burn. Other personal health information may indicate that user 2 has no family history of heart disease. Still other personal health information may indicate that user 2 is twenty-five-years old. Search engine 48 may use such personal health information to order search results 40 to generate personalized search results 40'. Search engine 48 may apply a machine learning algorithm or an artificial intelligence algorithm (not shown in FIG. 3) to search results 40 to generate personalized search results 40'. The machine learning algorithm or the artificial intelligence algorithm may be trained on health information of a large number of individuals (or living beings), symptoms, and the ultimate diagnoses for the condition that caused the symptoms. In this manner, search engine 48 may better order personalized search results 40' to place the most relevant (or more relevant) search hits at the top of personalized search results 40'.

For example, in the case of a potential heart attack or acid reflux, a k-means clustering model may be used having two clusters: one for a heart attack and one for acid reflux. Each user may be associated with a vector that includes variables for e.g., family history of GERD, family history of heart attack, cholesterol level, age, physical exercise level, etc.). The location of the vector in a given one of the clusters may be indicative of whether the user is experiencing a heart attack or acid reflux. For example, if the vector falls within the acid reflux cluster, the user is likely suffering from acid reflux, rather than a heart attack and search engine 48 may order personalized search results 40' with hits related to acid reflux at the top rather than hits related to heart attacks. Other potential machine learning techniques include k-nearest neighbors, support vector machines, neural networks, linear regression, logistic regression, Naïve Bayes, random forest, etc.

Search engine 48 may then send personalized search results 40' to be displayed to user 2 via computing device 4. For example, rather than displaying 11 pages of hits for heart attacks prior to showing GERD or acid reflux on page 12 (e.g., which may have been the way search results 40 was ordered), computing device 4 may display personalized search results 40' in which GERD or acid reflux may be displayed as the first hit. In this manner, user 2 may quickly see the most relevant or more relevant search results for the health condition of user 2.

According to the techniques of this disclosure, search engine 48 obtain search query 6. Search engine 48 may determine that search query 6 is health related. Based on (or in response to) the determination that the search query is health related, search engine 6 may determine a subject of search query 6, the subject of the search query being a living creature for whom a search is being performed. Based on (or in response to) the determination of the subject of search query 6, search engine 48 may determine health information of the subject of search query 6 (e.g., user 2) Search engine 48 may modify, based on the health information of the subject of search query 6, search query 6 to generate a modified search query (e.g., personalized search query 6') or an order of search results 40 to generate modified search results (e.g., personalized search results 40'). Search engine 48 may present search results 40 or modified search results 40' to user 2.

FIGS. 4A-4B are conceptual diagrams illustrating examples of search results and personalized search results according to one or more aspects of this disclosure. In the example of FIG. 4A search results 40 are shown. Because search query 6 of FIG. 2A stated "Am I having a heart attack?" search results 40 may display or otherwise provide to user 2 hits relating to heart attacks first. Thus, without ordering the search results based on personal health information, user 2 might be motivated to seek immediate medical attention even though it may be highly unlikely that user 2 is having a heart attack. For example, the first hit may even tell user 2 they are having a heart attack and tell user 2 to seek immediate medical attention. For example, results relating to heart attacks may occupy the first 11 pages of the search results and the first mention of GERD or acid reflux may be on page 12. In such cases, it is unlikely that user 2 may actually investigate the hits relating to GERD or acid reflux.

FIG. 4B show personalized search results 40' that are ordered based on the personal health information of user 2, the subject of search query 6. In this example, search engine 48 has organized search results 40' such that the more relevant hits are first. In this example, the GERD or acid reflux hits are first, thereby increasing the likelihood that user 2 will investigate the GERD or acid reflux hits and not seek immediate medical attention.

Figure 5:
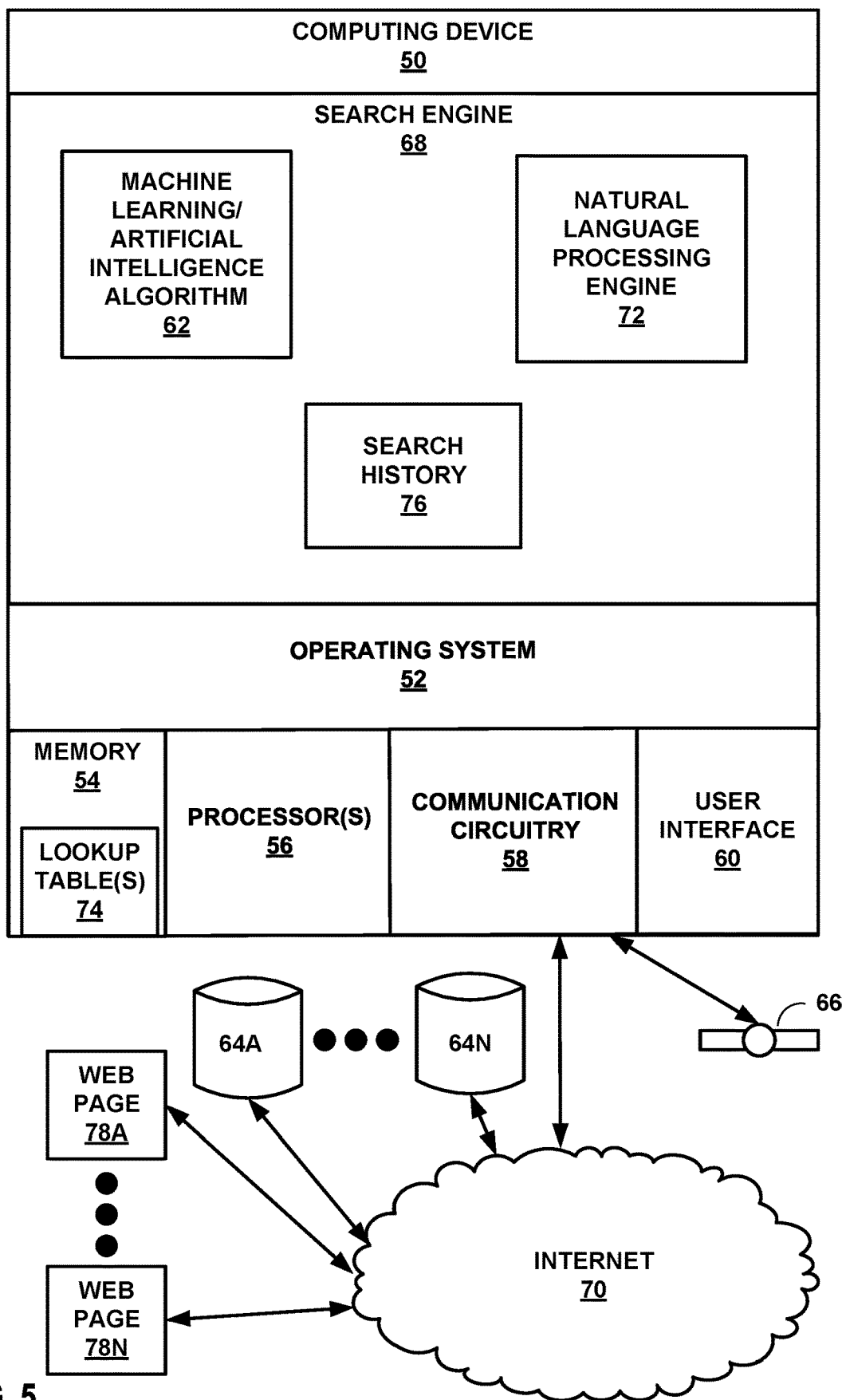
FIG. 5 is a block diagram illustrating an example computing device according one or more aspects of this disclosure.

FIG. 5 is a block diagram illustrating an example computing device 50 according one or more aspects of this disclosure. Computing device 50 may be an example of computing device 4 or may be an example of one or more servers located in a cloud computing environment. Computing device 50 may include memory 54 and one or more processor(s) 56 communicatively coupled to memory 54. In some examples, memory 54 and one or more processor(s) 56 may be integrated into a single hardware unit, such as a system on a chip (SoC). Each of one or more processor(s) 56 may include, be, or be part of one or more of a multi-core processor, a controller, a digital signal processor (DSP), an application specific integrated circuit (ASIC), a field-programmable gate array (FPGA), processing circuitry (e.g., fixed-function circuitry, programmable circuitry, or any combination of fixed function circuitry and programmable circuitry) or equivalent discrete logic circuitry or integrated logic circuitry. Memory 54 may include any form of memory for storing data and executable software instructions, such as random-access memory (RAM), read only memory (ROM), programmable read only memory (PROM), erasable programmable read only memory (EPROM), electronically erasable programmable read only memory (EEPROM), and flash memory. Memory 54 may store the software components of computing system 50 such as search engine 68. Memory 54 may also store one or more lookup table(s) 74 which may be used by search engine 68 to what health data may be relevant to search terms related to health as described above with respect to FIGS. 1 and 3. For example, heart burn may be relevant to a search for a heart attack. In some examples, one or more lookup table(s) 74 may include a list of entries with symptoms similar to those of a heart attack. Search engine 68 may look up the list of entries with symptoms similar to those of a heart attack and attempt to retrieve any available health information from databases 64A-64N and sensor 66 related to the list of entries. In some examples, one or more lookup table(s) 74 may include health-related terms, such as symptoms, diseases, medical conditions, context terms, such as "feel," etc., and one or more processor(s) 56 may look up search terms of search query 6 to determine if search query 6 is health related.

Memory 54 and one or more processor(s) 56 provide a computer platform for executing operation system 52. In turn, operating system 52 provides a multitasking operating environment for executing software components, such as search engine 68 and/or other software components. One or more processor(s) 56 may also be communicatively coupled to communication circuitry 58. Communication circuitry 58 may be configured to communicate with other devices (such as access points, gateways, routers, switches, etc., which are not shown for simplicity purposes) to access Internet 70 for searching purposes and to retrieve personal health information from external databases (such as databases 64A-64N), and/or web pages 78A-78N via Internet 70. Communication circuitry 58 may also be configured to retrieve personal health information from sensors (such as sensor 66 which may be an example of sensor 15 or sensor 35 of FIGS. 1 and 3, respectively), or the like, in order to retrieve personal health information.

In some examples, communication circuitry 58 may include wireless transmitters and receivers that enable computing device 50 to communicate wirelessly with other computing devices. Examples of communication circuitry 58 may include network interface cards, Ethernet cards, optical transceivers, radio frequency transceivers, or other types of devices that are able to send and receive information. Examples of communication circuitry 58 may include BLUETOOTH™, 3G, 4G, 5G, and WI-FI™ radios, Universal Serial Bus (USB) interfaces, etc. Computing device 50 may use communication circuitry 58 to communicate with one or more other computing devices or systems, such as sensor 66, or access point(s), gateways, switches, etc. (not shown) to access Internet 70, databases 64A-64N, web pages 78A-78N, or the like.

Computing device 50 may include user interface 60. User interface 60 may be configured to permit user 2 to enter search query 6 into search engine 68. For example, user interface 60 may include a keyboard, a virtual keyboard, mouse, display, touchscreen, microphone, speaker, or other device which may permit user 2 to enter information into computing device 50, such as search query 6, and receive information from computing device 50, such as personalized search results 40'.

Search engine 68 may include machine learning/artificial intelligence application 62, natural language processing engine 72 and/or search history 76. Machine learning/artificial intelligence application 62 may be a machine learning application, an artificial intelligence application or combination thereof. Machine learning/artificial intelligence application 62 may be trained on personal health information of a large number of individuals (or living beings), symptoms, and the ultimate diagnoses for the condition that caused the symptoms. Machine learning/artificial intelligence application 62 may be used by search engine 68 when ordering search results, such as personalized search results 40'. Search engine 68 may be configured to execute the techniques ascribed to search engine 28 of FIG. 1 and/or search engine 48 of FIG. 3. For example, search engine 68 may personalize a search query based on personal health information to include additional search terms and/or search engine 68 may personalize search results based on health information by ordering the search results to place more relevant results for the living being for whom the search is being performed at the beginning or top of the search results. Natural language processing engine 72 may be used by search engine 68 to determine whether a given search query is health related or not. For example, natural language processing engine 72 may be configured to discern between words that are health related and words that are not health related. In some examples, natural language processing engine may include an artificial intelligence or machine learning algorithm that may be trained to discern between words that are health related and words that are not health related. While shown in FIG. 5 as being part of search engine 68, in some examples, machine learning/artificial intelligence algorithm 62, natural language processing engine 72, and/or search history 76 may be separate from search engine 68.

Software components executing on computing device 50, such as search engine 68, represent executable software instructions that may take the form of one or more software applications, software packages, software libraries, hardware drivers, and/or Application Program Interfaces (APIs).

Figure 6:
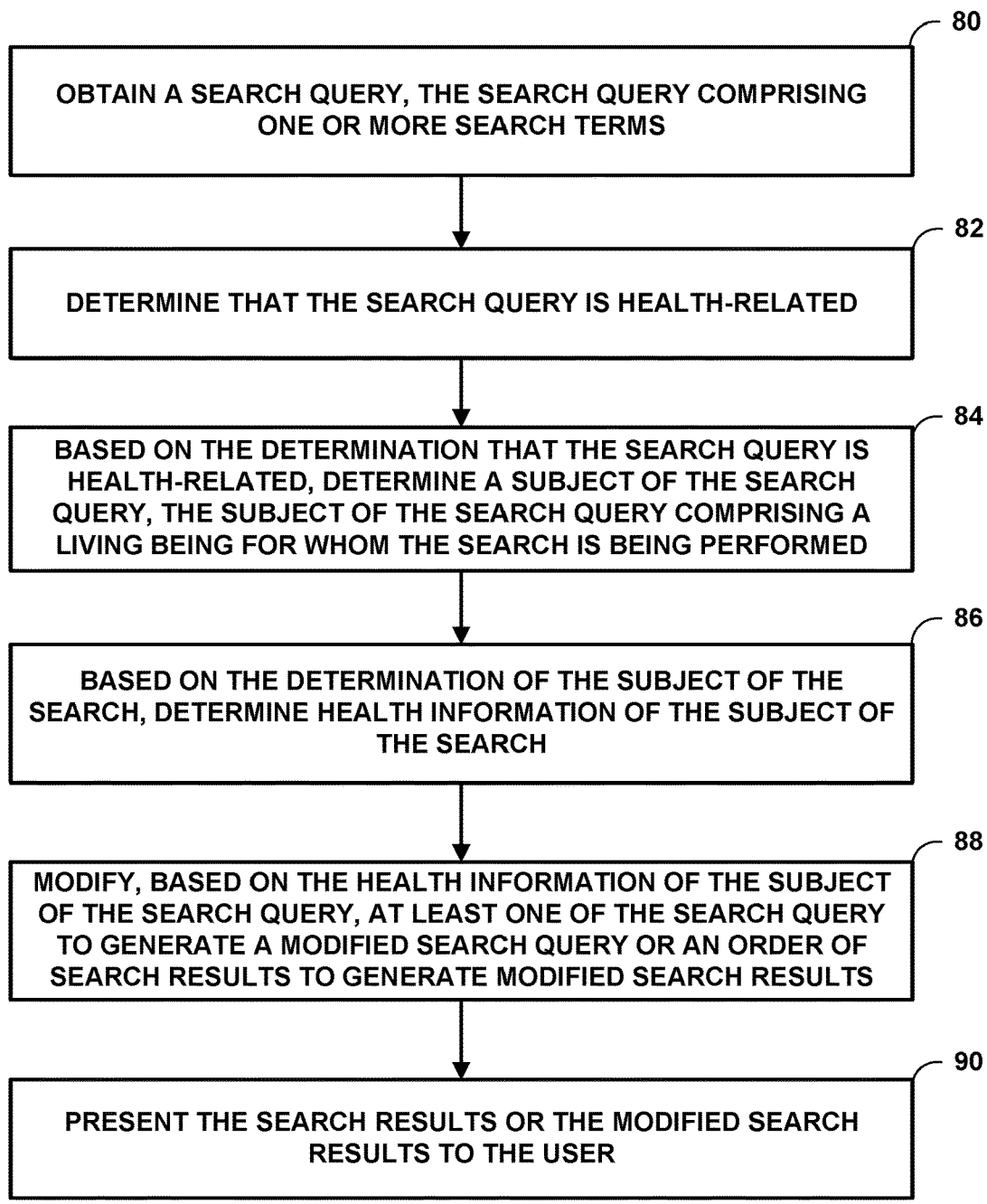
FIG. 6 is a flowchart illustrating example techniques of performing a personalized health search of the Internet or another network.

FIG. 6 is a flowchart illustrating example techniques of performing a personalized health search of the Internet or another network. The example of FIG. 6 is described with respect to computing device 50 of FIG. 5. However, the techniques of FIG. 6 may be performed by computing device 4, one or more servers, or a combination thereof.

One or more processor(s) 56 may obtain a search query, the search query comprising one or more search terms (80). For example, one or more processor(s) 56 may obtain search query 6 via user interface 60 from user 2.

One or more processor(s) 56 may determine that the search query is health related (82). For example, one or more processors 56 may use natural language processing engine 72 to determine whether search query 6 is health related.

One or more processor(s) 56 may, based on the determination that the search query is health related, determine a subject of the search query, the subject of the search query being a living creature for whom a search is being performed (84). For example, once one or more processor(s) 56 determine the search to be health related, one or more processor(s) 56 may determine whether the search is for user 2, a friend of user 2, a family member of user 2, a pet of user 2, a service animal of user 2, or the like. If the subject of the search query is not readily identifiable by one or more processor(s) 56, one or more processor(s) 56 may prompt user 2 via user interface 60 to enter additional information identifying the subject of search query 6.

Based on the determination of the subject of the search query, one or more processor(s) 56 may determine health information of the subject of the search query (86). For example, one or more processor(s) 56 may review search history 76 for past health-related searches, may communicate with sensor 66 to download biometric sensor data, and/or gather personal health information from one or more of databases 64A-64N and/or web pages 78A-78N (e.g., social media pages). In some examples, the health information may include data from electronic medical records, electronic health records, pharmacy data, claims data, family health history, demographic data, biometric sensor data, social determinates of health data, or online activity data.

One or more processor(s) 56 may modify, based on the personal health information of the subject of the search query, at least one of the search query to generate a modified search query or an order of search results to generate modified search results (88). For example, to modify the search query, one or more processor(s) 56 may determine one or more additional search terms to add to search query 6 based on the health information of the subject of the search query or remove one or more search terms from search query 6. One or more processor(s) 56 may add the one or more additional search terms to search query 6 or remove one or more search terms from search query 6 to generate the modified search query (e.g., personalized search query 6'). Alternatively, or additionally, for example, to modify the order of the search results, one or more processor(s) 56 may order search results 40 based on the health information of the subject of the search query to generate modified search results (e.g., personalized search results 40').

One or more processor(s) 56 may present the search results or the modified search results to the user (90). For example, one or more processor(s) 56 may present search results 26 (FIG. 1) or personalized search results 40' (FIG. 3) to user 2 via user interface 60.

In some examples, one or more processor(s) 56 may execute the search using the modified search query (e.g., personalized search query 6'). In some examples, one or more processor(s) 56 may execute the search using search query 6. In some examples, ordering search results 40 based on the health information of the subject of the search query comprises employing at least one of a machine learning algorithm or an artificial intelligence algorithm (e.g., machine learning/artificial intelligence algorithm 62) to order the search results to generate the modified search results (e.g., personalized search results 40'). In some examples, the health information comprises at least one of data from electronic medical records, pharmacy data, claims data, family health history, demographic data, biometric sensor data, or online activity data. In some examples, determining the subject of search query 6 comprises determining that search query 6 does not contain an indication of for whom the search is being performed, and based on search query 6 not containing an indication of for whom the search is being performed, prompting user 2 to enter an indication of for whom the search is being performed.

In some examples, determining that the search query is health related comprises one or more processor(s) 56 employing natural language processing engine 72 to analyze search query 6. In some examples, one or more processor(s) 56 may look up at least one of the one or more search terms in lookup table 74 and retrieve other health conditions or health symptoms which may be related to symptoms of the at least one of the one or more search terms from lookup table 74.

By providing a search engine or a search engine add-on application that may modify at least one of the search query or the order of search results, search results may be personalized to the living being for whom the search is being conducted, thereby improving the functioning of a computing device, lowering anxiety, saving healthcare costs, and reserving healthcare resources for those situations which are critical.

The techniques described in this disclosure may be implemented, at least in part, in hardware, software, firmware or any combination thereof. For example, various aspects of the described techniques may be implemented within one or more processors, including one or more microprocessors, DSPs, application specific integrated circuits (ASICs), field programmable gate arrays (FPGAs), processing circuitry (e.g., fixed function circuitry, programmable circuitry, or any combination of fixed function circuitry and programmable circuitry), or any other equivalent integrated logic circuitry or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

If implemented in software, the functions may be stored on or transmitted over a computer-readable medium as one or more instructions or code, and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), processing circuitry (e.g., fixed function circuitry, programmable circuitry, or any combination of fixed function circuitry and programmable circuitry), or other equivalent integrated logic circuitry or discrete logic circuitry, as well as any combination of such components. Accordingly, the term "processor," as used herein may refer to any of the foregoing structures or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wired or wireless communication device, a microprocessor, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A computer-implemented method comprising:
   receiving, by one or more processors, a search query, the search query comprising one or more search terms;
   determining, by the one or more processors, whether the search query is health related;
   in a first instance, in response to determining that the search query is health related:
      determining, by the one or more processors, a subject of the search query, the subject of the search query being a living creature for whom a first search is being performed, wherein determining the subject of the search query comprises determining that the search query does not contain an indication of for whom the first search is being performed, and based on the search query not containing the indication of for whom the first search is being performed, causing, by the one or more processors, a user interface to prompt a user to enter the indication of for whom the first search is being performed, the indication of for whom the first search is being performed being indicative of the subject of the search query; and
      causing, by the one or more processors, a search engine to perform the first search based on a modified search query including health information associated with the subject of the search query; and
   in a second instance, in response to determining that the search query is not health related, causing, by the one or more processors, the search engine to perform a second search based on only the search query.

2. The computer-implemented method of claim 1, wherein in the first instance, causing the search engine to perform the first search includes causing the search engine to arrange search results for display in an order based on at least a portion of the health information.

3. The computer-implemented method of claim 2, wherein in the first instance, causing the search engine to arrange the search results in the order based on at least the portion of the health information comprises employing at least one of a machine learning algorithm or an artificial intelligence algorithm to order the search results based on the at least the portion of the health information.

4. The computer-implemented method of claim 1, wherein the health information associated with the subject of the search query comprises at least one of data from electronic medical records, electronic health records, pharmacy data, claims data, family health history, demographic data, biometric sensor data, social determinates of health data, or online activity data.

5. The computer-implemented method of claim 1, wherein determining whether the search query is health related comprises employing a natural language processing engine to analyze the search query.

6. The computer-implemented method of claim 1, further comprising in the first instance:
- looking up, by the one or more processors, at least one of the one or more search terms in a database or a lookup table;
- retrieving, by the one or more processors, one or more other health conditions or health symptoms which are related to symptoms of the at least one of the one or more search terms from the lookup table; and
- generating, by the one or more processors, the modified search query, the modified search query comprising the one or more other health conditions or health symptoms.

7. A computing device comprising:
- a memory configured to store a search query comprising one or more search terms; and
- one or more processors implemented in circuitry and communicatively coupled to the memory, the one or more processors being configured to:
  - receive the search query;
  - determine whether the search query is health related;
  - in a first instance, in response to determining that the search query is health related:
    - determine a subject of the search query, the subject of the search query being a living creature for whom a first search is being performed, wherein, to determine the subject of the search query, the one or more processors are configured to determine that the search query does not contain an indication of for whom the first search is being performed, and based on the search query not containing the indication of for whom the first search is being performed, prompt a user to enter the indication of for whom the first search is being performed, the indication of for whom the first search is being performed being indicative of the subject of the search query; and
    - cause a search engine to perform the first search based on a modified search query including health information associated with the subject of the search query; and
  - in a second instance, in response to determining that the search query is not health related, causing the search engine to perform a second search based on only the search query.

8. The computing device of claim 7, wherein in the first instance, in order to cause the search engine to perform the first search, the one or more processors are configured to cause the search engine to arrange search results for display in an order based on at least a portion of the health information.

9. The computing device of claim 8, wherein in the first instance, to cause the search engine to arrange the search results in the order based on at least the portion of the health information, the one or more processors are configured to employ at least one of a machine learning algorithm or an artificial intelligence algorithm to order the search results based on the at least the portion of the health information.

10. The computing device of claim 7, wherein the health information associated with the subject of the search query comprises at least one of data from electronic medical records, electronic health records, pharmacy data, claims data, family health history, demographic data, biometric sensor data, social determinates of health data, or online activity data.

11. The computing device of claim 7, wherein to determine whether the search query is health related, the one or more processors are configured to employ a natural language processing engine to analyze the search query.

12. One or more non-transitory computer-readable storage media encoded with instructions that, when executed by one or more processors of a computing device, cause the one or more processors to:
- receive a search query, the search query comprising one or more search terms;
- determine whether the search query is health related;
- in a first instance, in response to determining that the search query is health related:
  - determine a subject of the search query, the subject of the search query being a living creature for whom a first search is being performed, wherein to determine the subject of the search query the instructions cause the one or more processors to determine that the search query does not contain an indication of for whom the first search is being performed, and based on the search query not containing the indication of for whom the first search is being performed, prompt a user to enter the indication of for whom the first search is being performed, the indication of for whom the first search is being performed being indicative of the subject of the search query; and
  - cause a search engine to perform the first search based on a modified search query including health information associated with the subject of the search query; and
- in a second instance, in response to determining that the search query is not health related, causing the search engine to perform a second search based on only the search query.

13. The one or more non-transitory computer-readable storage media of claim 12, wherein the instructions further cause the one or more processors to, in the first instance:
- look up at least one of the one or more search terms in a database or a lookup table;
- retrieve one or more other health conditions or health symptoms which are related to symptoms of the at least one of the one or more search terms from the lookup table; and
- generate the modified search query, the modified search query comprising the one or more other health conditions or health symptoms.

14. The computing device of claim 7, wherein the one or more processors are further configured to, in the first instance:
- look up at least one of the one or more search terms in a database or a lookup table;

retrieve one or more other health conditions or health symptoms which are related to symptoms of the at least one of the one or more search terms from the lookup table; and generate the modified search query, the modified search query comprising the one or more other health conditions or health symptoms.

\* \* \* \* \*